US011247963B2

(12) United States Patent
Ten Kate et al.

(10) Patent No.: US 11,247,963 B2
(45) Date of Patent: Feb. 15, 2022

(54) PROCESS FOR CONVERTING CYCLIC ALKYLENE UREAS INTO THEIR CORRESPONDING ALKYLENE AMINES

(71) Applicant: NOURYON CHEMICALS INTERNATIONAL B.V., Arnhem (NL)

(72) Inventors: Antoon Jacob Berend Ten Kate, Arnhem (NL); Rens Veneman, Amersfoort (NL); Hendrik Van Dam, Ede (NL); Rolf Krister Edvinsson, Partille (SE); Michiel Jozef Thomas Raaijmakers, Deventer (NL); Eike Nicolas Kantzer, Uddevalla (SE); Ina Ehlers, Stenungsund (SE); Slavisa Jovic, Utrecht (NL); Karl Fredrik Lake, Södertälje (SE); Stig Mikael Wernersson, Södertälje (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/638,351

(22) PCT Filed: Aug. 7, 2018

(86) PCT No.: PCT/EP2018/071326
§ 371 (c)(1),
(2) Date: Feb. 11, 2020

(87) PCT Pub. No.: WO2019/030196
PCT Pub. Date: Feb. 14, 2019

(65) Prior Publication Data
US 2020/0361852 A1 Nov. 19, 2020

(30) Foreign Application Priority Data
Aug. 11, 2017 (EP) .................................. 17186005

(51) Int. Cl.
*C07C 209/78* (2006.01)

(52) U.S. Cl.
CPC ................................. *C07C 209/78* (2013.01)

(58) Field of Classification Search
CPC .... C07C 209/78; C07C 209/62; C07C 209/86
See application file for complete search history.

(56) References Cited

U.S. PATENT DOCUMENTS

| 2,812,333 | A | * | 11/1957 | Steele | ................... C07D 233/32 548/323.5 |
| 3,640,052 | A | * | 2/1972 | Konoki | ................. C07C 273/10 95/12 |
| 4,283,255 | A | * | 8/1981 | Ramshaw | ................ B01D 3/30 159/6.1 |
| 4,387,249 | A | | 6/1983 | Harnden et al. | |
| 4,503,250 | A | | 3/1985 | Herdle | |
| 5,399,755 | A | | 3/1995 | Lagana | |
| 6,254,840 | B1 | * | 7/2001 | Mennen | ................. B01J 10/002 261/113 |
| 6,476,262 | B2 | * | 11/2002 | Fukunaka | ............ B01D 5/0012 564/67 |
| 10,376,859 | B2 | * | 8/2019 | Coloma Gonzalez | . B01D 5/006 |
| 10,428,010 | B2 | * | 10/2019 | Edvinsson | ........... C07D 233/36 |
| 10,781,167 | B2 | * | 9/2020 | Rugnone | ................ B01D 1/065 |
| 10,800,731 | B2 | * | 10/2020 | Veneman | ............. C07D 263/20 |
| 10,844,001 | B2 | * | 11/2020 | Edvinsson | ........ C07C 273/1809 |
| 10,941,427 | B2 | * | 3/2021 | Kishino | ................ C01C 1/0411 |
| 10,975,017 | B2 | * | 4/2021 | Kantzer | ............... C07D 233/36 |
| 2004/0127608 | A1 | * | 7/2004 | Pardoen | ................. C08G 73/02 524/88 |

(Continued)

FOREIGN PATENT DOCUMENTS

| CN | 1073152 A | 6/1993 | |
| EP | 0053410 A1 | * 6/1982 | ................ C02F 9/00 |
| EP | 0053410 A1 | 6/1982 | |
| EP | 0538848 A1 | * 4/1993 | ............. C02F 1/025 |

(Continued)

OTHER PUBLICATIONS

D. Rao et al., 43 Ind. Eng. Chem. Res., 1150-1162 (2004) (Year: 2004).*
R. de Graaf et al. "A dynamic model for the Venturi Loop Reactor Venturi loop reactor", Scientific Computing in Chemical Engineering II 239-246 (Springer, 1999) (Year: 1999).*
EPO, European Extended Search Report issued in European Application No. 17186005.9, dated Jan. 3, 2018.
EPO, International Search Report and Written Opinion issued in International Application No. PCT/EP2018/071326, dated Sep. 25, 2018.

(Continued)

*Primary Examiner* — Alexander R Pagano
(74) *Attorney, Agent, or Firm* — Lorenz & Kopf, LLP

(57) ABSTRACT

A process is provided for converting one or more cyclic ethylene ureas into corresponding ethylene amines and carbon dioxide. The process may include contacting water with one or more cyclic alkylene urea compounds comprising one or more cyclic alkylene urea moieties in a reaction vessel at a temperature of 150 to 400° C., optionally in the presence of an amine compound selected from the group of primary amines, cyclic secondary amines and bicyclic tertiary amines. The mole ratio of water to cyclic alkylene urea moieties is in the range of from about 0.1 to about 20. In the reaction, at least a portion of the cyclic alkylene urea moieties are converted to corresponding alkylenediamine moieties and carbon dioxide. The process may further include removing the carbon dioxide from the liquid reaction mixture in a stripping vessel by feeding a stripping fluid to the stripping vessel. Further, the process may include removing a carbon dioxide-containing stripping fluid.

14 Claims, 1 Drawing Sheet

(56) References Cited

U.S. PATENT DOCUMENTS

| | | | | |
|---|---|---|---|---|
| 2008/0281126 | A1* | 11/2008 | Kohler | C07C 209/62 |
| | | | | 564/468 |
| 2011/0015439 | A1* | 1/2011 | Hanson | C07C 209/16 |
| | | | | 564/475 |
| 2019/0031597 | A1* | 1/2019 | Edvinsson | C07C 273/1809 |
| 2019/0039993 | A1* | 2/2019 | Edvinsson | C07C 269/06 |
| 2019/0039994 | A1* | 2/2019 | Edvinsson | C07C 209/62 |
| 2019/0308930 | A1* | 10/2019 | Kantzer | C07C 209/62 |
| 2020/0165187 | A1* | 5/2020 | Ten Kate | C07C 209/86 |
| 2020/0165207 | A1* | 5/2020 | Kantzer | C07D 233/34 |
| 2020/0199060 | A1* | 6/2020 | Ten Kate | C07C 209/62 |
| 2020/0361850 | A1* | 11/2020 | Kantzer | C07C 213/02 |
| 2020/0361851 | A1* | 11/2020 | Veneman | C07C 209/86 |
| 2020/0362111 | A1* | 11/2020 | Veneman | C07C 209/68 |

FOREIGN PATENT DOCUMENTS

| | | | | |
|---|---|---|---|---|
| EP | 0538848 | A1 | 4/1993 | |
| WO | WO-2017137529 | A1 * | 8/2017 | ........... C07D 233/36 |
| WO | WO-2019030190 | A1 * | 2/2019 | ........... C07C 209/62 |

OTHER PUBLICATIONS

Schmidt, S. et al., "Absorption, 2. Design of Systems and Equipment", • Ullmann's Encyclopedia of Industrial Chemistry, in the chapter Absorption, 2, Design of Systems and Equipment, 2012, pp. 73-90.

Fair, J.R., et al. "Gas Absorption and Gas-Liquid System Design", Perry's Chemical Engineer's Handbook, 1999, pp. 14-1-14-98.

* cited by examiner

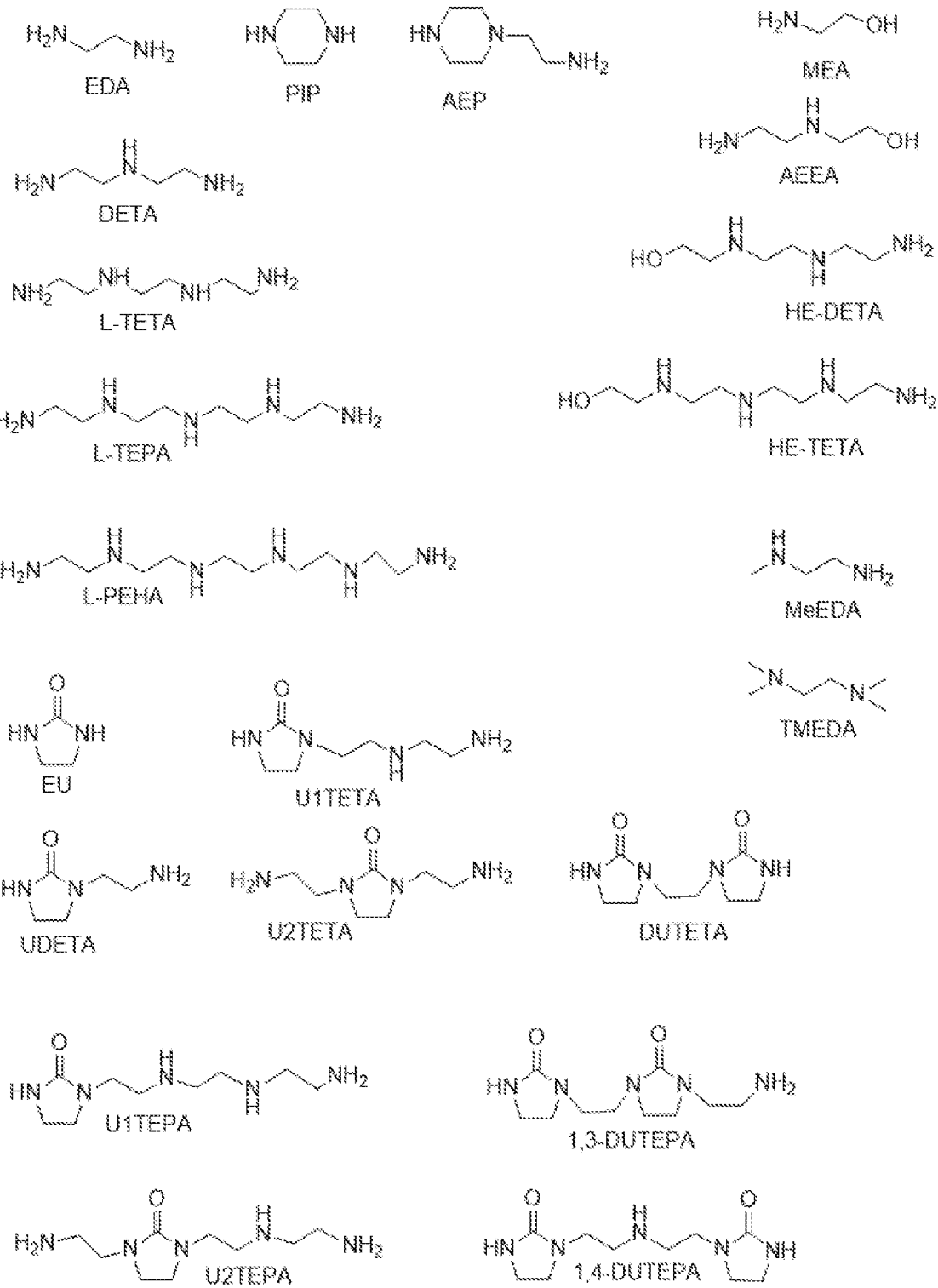

PROCESS FOR CONVERTING CYCLIC ALKYLENE UREAS INTO THEIR CORRESPONDING ALKYLENE AMINES

CROSS-REFERENCE TO RELATED APPLICATION

This application is a U.S. National-Stage entry under 35 U.S.C. § 371 based on International Application No. PCT/EP2018/071326, filed Aug. 7, 2018, which was published under PCT Article 21(2) and which claims priority to European Application No. 17186005.9, filed Aug. 11, 2017, which are all hereby incorporated in their entirety by reference.

TECHNICAL FIELD

The present invention relates to a process for converting cyclic alkylene ureas into corresponding alkyleneamines.

BACKGROUND

Cyclic alkylene ureas are compounds comprising one or more cyclic alkylene urea moieties, in which two nitrogen atoms are connected by a carbonyl moiety and an alkylene moiety. For example, cyclic ethylene urea comprises two nitrogen atoms connected by a carbonyl moiety and an ethylene moiety, i.e.

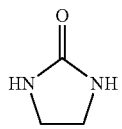

Cyclic alkylene urea compounds can be converted into the corresponding alkylene amines by removal of the CO group(s) and addition of two hydrogen atoms. Carbon dioxide is produced. The removal of the carbonyl group from the cyclic alkylene urea to produce carbon dioxide is sometimes referred to as "desorption", or "reactive desorption", and sometimes referred to as a "decarbonylation" reaction.

Alkylene amines, in particular ethylene amines, specifically in particular diethylene triamine (DETA) and higher ethylene amines such as triethylene tetramine (TETA) are attractive products from a commercial point of view. Cyclic ethylene ureas are therewith an attractive intermediate in the manufacture of ethylenediamine and higher ethyleneamines.

It has been found, however, that cyclic ethylene ureas are relatively stable. It is quite difficult to convert cyclic ethylene urea compounds into ethylene amines in high yield. This goes in particular for compounds where the ethylene urea moiety is connected to further ethylene amine or alkyl moieties via the nitrogen atoms, in particular where the ethylene urea moiety is present between two further ethylene amine moieties.

The difficulty in converting the cyclic ethylene ureas to ethylene amines can also be seen from the prior art, where the conversion is carried out with large excesses of strong inorganic bases.

U.S. Pat. No. 4,503,250 describes a process for preparing linear polyalkylene polyamines which comprises reacting ammonia or an alkyleneamine compound having two primary amino groups or mixtures thereof with an alcohol or an alkanolamine compound having a primary amino group and a primary or secondary hydroxyl group or mixtures thereof in the presence of a derivative of carbonic acid at a temperature at which the reaction will proceed under pressures sufficient to maintain the reaction mixture substantially in a liquid phase. The process results in the formation of urea adducts of polyalkylene polyamines. The urea adducts are converted to polyethylene polyamines by reaction with 50% aqueous KOH under reflux overnight. 8 moles KOH are used per mole carbon dioxide.

U.S. Pat. No. 4,387,249 discloses the reaction of ethylenediamine (EDA), ethanolamine (MEA) and urea to give aminoethylethyleneurea (UDETA) and ethyleneurea (EU), which are hydrolysed to form DETA and EDA. The hydrolysis step takes place in an inert atmosphere in the presence of a Brønsted base. The Brønsted base preferably is the hydroxide of an alkali metal, more preferably an aqueous solution of NaOH. In the examples hydrolysis takes place at a temperature of 200° C. under autogenous pressure, using a 5 mole/liter NaOH solution.

While quite effective, the process as described in these references has a number of disadvantages. The use of caustic bases at elevated temperatures has as a disadvantage that it might result in low product selectivities due to degradation of the desired products. In addition, when using an (inorganic) base, salts are formed as by-products which complicate the following separation of organics, resulting in lower yields of the targeted product. In addition the combination of amines, water, salt and high temperatures can cause problems with corrosion, discolored products and decreased storage stability. Further, an outlet has to be found for processing the large amounts of salts.

U.S. Pat. No. 2,812,333 describes the hydrolysis of 1-(2-hydroxyethyl)imidazolinone-2 to the corresponding hydroxyethylethylenediamine by heating in the presence of water at elevated temperatures, with removal of $CO_2$. The reaction takes place in a large excess of water; in the example a 12% solution of the 1-(2-hydroxyethyl)imidazolinone-2 is used. The conversion is low. Under test conditions approximately 5% of the compound hydrolysed per hour.

There is need in the art for a process for converting cyclic ethylene ureas into their corresponding ethylene amines which combines a high conversion of cyclic ethylene ureas into the corresponding amines, while addressing the disadvantages of the prior art processes.

In addition, other objects, desirable features and characteristics will become apparent from the subsequent summary and detailed description, and the appended claims, taken in conjunction with the accompanying drawings and this background.

SUMMARY

A process is provided for converting one or more cyclic ethylene ureas into corresponding ethylene amines and carbon dioxide. The process may include contacting water with one or more cyclic alkylene urea compounds comprising one or more cyclic alkylene urea moieties in a reaction vessel at a temperature of from about 150 to about 400° C., optionally in the presence of an amine compound selected from the group of primary amines, cyclic secondary amines and bicyclic tertiary amines, the mole ratio of water to cyclic alkylene urea moieties being in the range of from about 0.1 to about 20, wherein at least a portion of the cyclic alkylene urea moieties are converted to corresponding alkylenediamine moieties and carbon dioxide. Also, the process may include removing carbon dioxide from the liquid reaction mixture in a stripping vessel by feeding a stripping fluid to the stripping vessel. Further the process may include removing a carbon dioxide-containing stripping fluid.

In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

More generally, the invention relates to a process for converting cyclic alkylene ureas into their corresponding alkylene amines.

A cyclic alkylene urea compound can have one cyclic alkylene urea moiety (an example being ethylene urea), or more than one cyclic alkylene urea moiety (an example being 1,2-bis(ethyleneurea)ethane, otherwise known as DUTETA).

In the process, a reaction mixture comprising one or more cyclic alkylene ureas and water are contacted in a reaction zone at a temperature in the range of from 150 to 400° C. The mole ratio of water to the one or more cyclic alkylene urea moieties is in the range of from 0.1 to 20. The reaction results in at least a portion of the cyclic alkylene urea moieties being converted to corresponding alkylenediamine groups. Optionally an amine compound selected from the group of primary amines, cyclic secondary amines, and bicyclic tertiary amines can also be present in the reaction mixture.

The CO2 formed in the process is separated from the reaction mixture using a stripping fluid in a stripping vessel, in which the stripping fluid is fed to the stripping vessel, and a $CO_2$-containing stripping fluid is removed from the stripping vessel. The stripping vessel can be the same as or different from the reaction vessel in which the reaction takes place.

BRIEF DESCRIPTION OF DRAWINGS

The present invention will hereinafter be described in conjunction with the following drawing FIGURES, wherein like numerals denote like elements, and:

FIG. 1 shows molecular structures of a number of cyclic alkylene ureas and alkylene amines.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

In the process of the present invention, cyclic alkylene urea moieties are converted to corresponding alkylene amine groups. CO2 is formed, which is removed using a stripping fluid. The invention is particularly advantageous, since it can improve the total decarbonylation of cyclic alkylene ureas through to their corresponding alkylene amines, even when the cyclic alkylene ureas comprise more than one cyclic alkylene urea moiety (as is the case, for example, in the molecule DUTETA).

In embodiments, the reaction can involve adding an inorganic base. This helps to further convert cyclic alkylene urea moieties that remain after the first step into corresponding alkylene amines, although overall there is less usage of inorganic base compared to prior art methods, for example.

The reaction mixture comprises one or more cyclic alkylene ureas. These are compounds comprising at least one occurrence of two nitrogen atoms connected by a carbonyl group and an alkylene group. In embodiments, the cyclic alkylene ureas are compounds of Formula I:

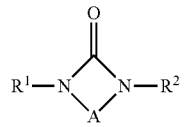

Formula I

A is on each occurrence independently selected from $C_1$ to $C_3$ alkylene units, optionally substituted by one or more $C_1$ to $C_3$ alkyl groups.

$R^1$ and $R^2$ are each independently selected from $-[A-X^1-]_qR^3$.

$R^3$ is on each occurrence independently selected from H and $C_1$ to $C_{20}$ alkyl groups, which are optionally substituted by one or two groups selected from $-OH$ and $-NH_2$.

$X^1$ is on each occurrence independent selected from $-O-$, $-NR^3-$, groups of Formula II, and groups of Formula III:

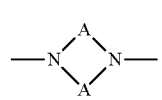

Formula II

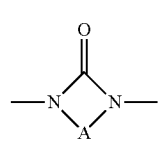

Formula III

If at least one $X^1$ is a group of Formula III, the compound of Formula I comprises more than one cyclic alkylene urea moiety.

Each q is independently selected from a whole number in the range of from 0 to 20, for example from 0 to 8, such as from 0 to 6.

In embodiments, at least one A is an unsubstituted C2-C3 alkylene. In further embodiments, all A are selected from unsubstituted C2-C3 alkylene. In other embodiments, at least one A is an optionally substituted C2 alkylene, and in further embodiments all A are optionally substituted C2 alkylene. In other embodiments at least one A is an unsubstituted C2 alkylene, and in further embodiments all A are unsubstituted C2 alkylene.

In embodiments, each R3 is selected from H and C1 to C3 alkyl (e.g. C2 alkyl) optionally substituted with one NH2 or OH group. Where there is a substituent, it is preferably an NH2 group. In embodiments, R3 is hydrogen.

In embodiments, each q is selected from a whole number in the range of from 0 to 3, for example from 0 to 2. In further embodiments, at least one occurrence of q is 1.

In embodiments, X1 is selected from NR3 and cyclic groups of Formula II and Formula III.

In embodiments, no more than one X1 group is a cyclic group selected from groups of Formula II and Formula III. In further embodiments, no X1 group is a cyclic group of Formula II or Formula III.

In embodiments, R1 is a hydrogen atom, and R2 is not a hydrogen atom. In further embodiments, the R2 contains a repeating alkylene amine group (i.e. -[A-NR3-]q-), where in embodiments R3 is H. Even more preferably, R2 contains a repeating ethylene amine group (i.e. —[CH2-CH2-NR3-]q-), wherein embodiments R3 is H. In these embodiments, optionally one or more of the —X1- groups is a cyclic moiety of formula II or III, in which A is optionally —CH2CH2-.

Some examples of cyclic alkylene ureas that are most preferred are EU (ethyleneurea), UDETA (the urea of diethylenetriamine), UTETA (the ureas of triethylenetetraamine, i.e. U1TETA or U2TETA, dependent on whether the urea is between the 1st and 2nd amine in the chain or 2nd and 3rd amine, respectively), DUTETA (the diurea of triethylenetetramine), UTEPA (the ureas of tetraethylenepentamine, i.e. U1TEPA, U2TEPA depending on where the urea unit is located), DUTEPA (DU1,3TEPA, DU1,4TEPA, the diureas of tetraethylenepentamine), UAEEA (the urea of aminoethylethanolamine), HE-UDETA (the urea of hydroxyethyl diethylenetriamine, that can exist in two isomers HE-U1-DETA and HE-U2DETA), HE-UTETA (the urea of hydroxyethyl triethylenetetraamine, that can exist in three isomers HE-UTETA, HE-U2TETA and HE-U3TETA), HE-DUTETA (the diurea of hydroxyethyl triethylenetetraamine), or any mixture of these. The molecular structures of a number of the above cyclic alkylene ureas are given in FIG. 1. To avoid any confusion, if a number is given for the amine group where the cyclic urea unit U is located, the amine groups are counted from the terminal amine group on the molecule which in the case of hydroxyethylated ethylene amines is the amine group at the end not containing the hydroxyl group.

In addition to carbon dioxide, compounds of Formula IV are produced:

$$R^4\text{—HN-A-NH—}R^5 \qquad \text{Formula IV}$$

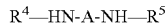

$R^4$ and $R^5$ are each independently selected from $\text{-[A-X}^2\text{-]}_q R^3$.

$X^2$ is as defined above for $X^1$, and can also be selected from —NH-A-NH—. This group is formed from decarbonylation of a group of Formula III.

A, $R^3$ and q are as defined above.

In embodiments, at least one of the groups of Formula III are converted to —NH-A-NH—. In further embodiments, all groups of Formula III are converted to —NH-A-NH—.

In the reaction, at least a portion of the carbonyl groups of the cyclic alkylene urea moieties are ultimately converted to carbon dioxide. The carbon dioxide is removed during the reaction. This can be achieved using a stripping fluid, e.g. a gas or a liquid. If a liquid is used, it is generally a liquid that is immiscible with the reaction mixture.

In embodiments, improved yields of fully decarbonylated cyclic alkylene ureas are achieved, i.e. the cyclic alkylene ureas are converted more effectively to the corresponding alkylene amines, where all cyclic alkylene urea moieties have been converted to alkylene amine moieties. The so-produced alkylene amines are of Formula IV, where the X2 group is selected from —O—, —NR3- and —NH-A-NH—.

Depending on the reaction temperature and the desired degree of conversion, the reaction time can vary within wide ranges, e.g., at least one minute, in particular at least 5 minutes, more in particular between 15 minutes and 24 hours. In one embodiment, the reaction time may be at least 30 minutes, or at least 1 hour. It may be preferred for the reaction time to vary between 1 hour and 12 hours, in particular between 1 hour and 6 hours. When using lower temperatures, longer reaction times may be required to obtain the desired degree of conversion.

Conversion with water does not rely on the use of an inorganic base. However, a limited amount can be present if desired. A strong inorganic base for the purposes of the invention is a material which does not contain carbon-carbon bonds, and which has a pKb of less than 1. In one embodiment, the strong inorganic base (if used) is selected from the group of metal hydroxides, in particular from alkali and alkaline earth metal hydroxides, more particularly from sodium hydroxide, potassium hydroxide, lithium hydroxide, calcium hydroxide, magnesium hydroxide and barium hydroxide. Selecting a strong inorganic base from sodium hydroxide, potassium hydroxide, magnesium hydroxide and calcium hydroxide may be preferred. The use of sodium hydroxide and/or potassium hydroxide may be particularly preferred. Ammonium hydroxide is another example of a strong inorganic base that can be used. One or more than one strong inorganic bases can be used.

If an inorganic base is used, it is generally used in an amount of less than 0.5 moles per mole cyclic alkylene urea moiety, in particular less than 0.2 mole inorganic base per mole cyclic alkylene urea moiety.

In one embodiment, the process is carried out by reacting the cyclic alkylene ureas in the liquid phase with water in an amount of 0.1 to 20 moles water per mole cyclic alkylene urea moiety, at a temperature of at least 200° C., or at least 230° C. It has been found that the use of a low amount of water in combination with a relatively high temperature in combination with $CO_2$ removal results in an efficient process with good conversion and low formation of side products.

The amount of water present depends on the desired degree of conversion and on the process conditions. Although good conversion can be achieved with a relatively limited amount of water of 20 moles per mole cyclic alkylene urea moiety, lower amounts of water can also be used, for example at most 15 moles water per mole cyclic alkylene urea moiety, in particular at most 10 mole water per mole cyclic alkylene urea moiety, or even at most 5 moles per mole cyclic alkylene urea moiety.

The range of 0.1 to 20 moles water per mole cyclic alkylene urea moieties refers to the amount of water added during the process, calculated on the amount of urea moieties in the feedstock at the start of the reaction. To obtain full conversion, 1 mole of water is required per mole cyclic urea moiety to be converted. As full conversion is not always necessary, lower amounts of water can be used. Therefore, water is used in an amount of at least 0.1 mole per mole cyclic alkylene moiety. Higher amounts are often used, for example at least 0.2 mole per mole cyclic alkylene urea moiety, in particular at least 0.5 mole water per mole cyclic alkylene urea moiety.

Water can be added at the beginning of the process in a single dose. It is preferred, however, to add the water during the process in several doses, or continuously. In a continuous operation, multiple feedpoints can be used. By matching the amount of water added to the amount of water consumed by the reaction, the excess water in the reaction can be limited. It has been found that this limits the formation of side products.

The mole ratio of water to cyclic alkylene urea moieties is calculated on the water present in the reaction medium. Water can be added as a liquid. Water can instead, or also, be added in the form of steam, which can be advantageous in that heat is also added to the reaction mixture. Where steam is added, the majority of water in the steam will typically not be absorbed in the liquid reaction medium. The skilled person can regulate the conditions of water and/or steam addition in such a way that the desired amount of water is absorbed by the reaction medium. The water can also be present in the feedstock at the beginning of the desorption process, e.g. as a result of its presence in the process by which the cyclic alkylene urea-containing feedstock was produced.

Where water is added, the reaction is typically performed at a temperature of at least 150° C., for example at least 180° C. or at least 200° C. In embodiments, the temperature is at least 230° C. At lower temperatures, the reaction rate is typically too low to obtain meaningful conversion in an acceptable time frame. It is preferred to carry out the reaction at a temperature of at least 240° C., in particular at least 250° C. The maximum temperature is typically 400° C. It may be preferred to carry out the reaction at a temperature of at most 350° C., in particular at most 320° C.

Where water is added, the pressure is not critical, as long as the reaction mixture is in the liquid phase. As a general range, a value of 0.5 to 100 bara (bar-absolute) can be used, depending on the desired temperature. It is preferred for the CO2 removal step to be carried out at a pressure of at least 5 bar, in particular at least 10 bar, to maintain a sufficient amount of amine and water in the medium. In view of the high costs associated with high-pressure apparatus, it may be preferred for the pressure to be at most 50 bar, in particular at most 40 bar.

If so desired the reaction can be carried out with water in the presence of an amine compound selected from the group of primary amines, cyclic secondary amines, and bicyclic tertiary amines.

Primary amines are amine functional compounds in which the amine group is of the formula R6-NH2 and wherein R6 can be any organic group, preferably an aliphatic hydrocarbon with optional heteroatoms such as oxygen and/or nitrogen. Secondary cyclic amines are amines of the formula $R^7$—NH—$R^8$, wherein $R^7$ and $R^8$ together form a hydrocarbon ring, optionally with heteroatoms such as oxygen and/or nitrogen, preferably a piperazine ring. Tertiary bicyclic amines are amines of the formula $R^9$—N(—$R^{11}$)—$R^{10}$ where $R^9$ and $R^{10}$ together form a hydrocarbon ring—optionally with heteroatoms such as oxygen and/or nitrogen—and $R^9$ and $R^{11}$ together form another hydrocarbon ring—optionally with heteroatoms such as oxygen and/or nitrogen. On all the above groups $R^6$ to $R^{11}$ substituents can be present, such as alkyl or hydroxyalkyl groups. Primary amines, cyclic secondary amine and bicyclic tertiary amines all contain a sterically relatively unhindered amine group. In this document a compound is defined as a primary amine or a secondary cyclic amine or a tertiary bicyclic amine if one of the amine groups in the compound is a primary amine or secondary cyclic amine or a tertiary bicyclic amine group, independent of if this compound contains further amine groups that may be different in their nature. A compound can also contain two or more different amine functionalities, e.g. a primary amine and a secondary cyclic amine functionality or a primary amine, a secondary cyclic amine and a tertiary bicyclic amine functionality.

Preferred examples of primary amines are alkylamines, linear ethylene amines, and alkanolamines. Preferred examples of cyclic secondary amines are amines that contain a terminal piperazine ring. Preferred examples of bicylic tertiary amines are 1,4-diazabicyclo[2.2.2]octane (DABCO), 1,4-diazabicyclo[2.2.2]octan-2-yl)methanol and 1-azabicyclo[2.2.2]octane (Quinuclidine).

The amine compound is preferably a compound with more than one amine group wherein at least one of the amine groups is a primary amine, even more preferably it is an amine wherein two amine groups are a primary amine. The amine compound is preferably a compound different than the compound of Formula IV that can be obtained by the process of the invention.

In another preferred embodiment the amine compound is a compound that can bind with the carbonyl group from the cyclic alkylene urea. Preferred amine compounds include an alkylene amine, or an alkanol amine compound, even more preferably a smaller alkylene amine such as ethylene amine, or alkanol amine such as ethanolamine. In embodiments, they can be selected from ethylenediamine (EDA), diethylenetriamine (DETA), monoethanolaomine (MEA), aminoethylethanolamine (AEEA), N-aminoethylpiperazine (AEP), N, N'-diaminoethylpiperazine (DAEP), UDETA, N,N'-diaminoethyl-2-imidazolidinone (U2TETA), tris-aminoethylamine (TAEA).

In yet another preferred embodiment the amine compound is a compound that binds the carbonyl group from the cyclic alkylene urea to give among others another linear or cyclic alkylene urea or linear or cyclic alkylene carbamate, which is larger or less volatile than the alkylene amine of Formula IV formed by the process of the invention. In other preferred embodiments, the amine is solid under the conditions used to work up the reaction mixture or is bound to a solid carrier. Examples thereof are DETA-PS (i.e. a diethylene triamine linked to a solid polystyrene) or a solid polyethyleneimine (PEI).

Preferred amine compounds that can be used in the CO2 removal step of the process according to the invention include ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), 1,4-diazabicyclo[2.2.2]octane (DABCO), 1,4-diazabicyclo[2.2.2]octan-2-yl)methanol, triethylenetetramine (TETA), N-diethyldiamine-2-imidazolidinone (UTETA), N, N'-diaminoethylpiperazine (DAEP), N, N'-diaminoethyl-2-imidazolidinone (U2TETA), tetraethylenepentamine (TEPA), pentaethylenehexamine (PEHA), and the mono cyclic ureas of TEPA and PEHA (i.e. U1TEPA, U2TEPA, U1PEHA, U2PEHA, U3PEHA) and the dicyclic urea isomers of PEHA (i.e. DUPEHA), a polyethyleneimine (PEI) or an alkylene amine on a solid carrier.

The amine compound is preferably dosed in a molar amount of between 0.001 and 100 equivalents in regard to the total molar amount of cyclic alkylene urea, more preferably between 0.01 and 50 equivalents, even more preferably between 0.05 and 30 equivalents, yet more preferably between 0.15 and 25 equivalent and most preferably between 0.20 and 20 equivalents.

It is preferred for the feed to the process according to the invention to consist for at least 70 wt. % of the total of water, cyclic alkylene ureas, in particular those indicated above as preferred, and if present, amine compounds selected from the group of primary amines, cyclic secondary amines, and bicyclic tertiary amines, in particular those indicated above as preferred. It is particularly preferred for the composition provided to the first step to consist for at least 80 wt. % of the total of these compounds, more in particular for at least 90 wt. %.

The reaction with water and amine compound in one embodiment is generally performed for a time of at least 1 minute, preferably at least 15 minutes, and in embodiments for at least 1 hour. The reaction time is typically 24 hours or less, for example 12 hours or less. Preferably the reaction is run in less than 10 hours, more preferably in less than 8 hours, most preferably less than 5 hours. As a skilled person will understand this reaction time does not include any further processing of the reaction mixture such as for separating the obtained compounds.

In a preferred embodiment, in the first step of the process according to the invention a cyclic ethylene urea of TETA or TEPA, such as linear TETA diurea (DUTETA) or linear TEPA diurea (DUTEPA), is converted to linear TETA (L-TETA) or linear TEPA (L-TEPA) by employing an amine selected from the group of EDA, DETA, MEA, AEEA, N-methyl-EDA (MeEDA), AEP, DAEP, U2TETA, and TAEA. Particularly preferred are the amine compounds EDA, DETA, U2TETA, DAEP or AEP. The conversion of DUTETA with EDA and water proceeds preferably between 150 and 350° C., preferably between 200 and 300° C.

In the desorption process, $CO_2$ is removed from the system. The system comprises other volatile compounds such as water and in some embodiments low-boiling amines. The $CO_2$ removal focuses on the removal of $CO_2$, and while evaporation of other volatiles may not be detrimental, it will generally be limited.

It has been found that mass transfer (i.e. rate of transfer of $CO_2$ from the liquid reaction mixture into the separation fluid) can strongly influence both the capacity of the process, and the selectivity to desired alkylene amine products of Formula IV. Therefore, process equipment can be selected accordingly that will help improve the yields of alkylene amines of Formula IV, and can also help reduce reaction times. It is thought that reducing the residence time of carbon dioxide in the liquid phase can increase the possibility of side reactions in the reaction mixture, for example carbonylation reactions that insert carbonyl groups between two amino groups that are in close proximity to each other, and hence which re-introduce urea groups into the alkylene amine molecules.

A stripping fluid is used to assist removal of $CO_2$ from the reaction mixture. In one embodiment, this can be achieved by removing part of the reaction mixture, heating to vapourise solvent (e.g. water), and feeding the vapourised solvent back to the reaction mixture as a stripping vapour or gas. In another embodiment, one or more extraneous inert stripping gases can be fed through the reaction mixture. Examples of inert stripping gases include nitrogen, methane, helium and argon.

Stripping operations can be carried out in suitably adapted vessels or columns. In embodiments, the reaction takes place in a reaction vessel, and the reaction mixture fed batchwise, semi-continuously or continuously to a stripping vessel, optionally with recycle of the treated liquid phase back to the reaction vessel. In preferred embodiments, the stripping vessel also acts as the reaction vessel, such that the reaction mixture is contacted with stripping fluid during the course of reaction.

The use of gas phase stripping fluids are preferred. In stripping vessels suitable for gas-phase stripping, gas-liquid contact is facilitated by the column comprising plates or packing elements, which act as an interfacial surface through which the mass transfer takes place.

Flow of stripping gas and liquid reaction mixture can be staged, cocurrent, counter-current or cross-flow. Cross-flow and countercurrent modes are preferred.

When contacting stripping gas and liquid reaction mixture, either the gas or the liquid can be in a continuous phase. For example, droplets of liquid can be contacted with a continuous gas phase. In other embodiments, gas can be fed to or bubbled through a continuous liquid phase.

In one embodiment, the stripping vessel or reaction vessel is adapted with plates, and is configured to operate in countercurrent flow or cross-flow mode using a liquid or gas continuous phase.

In another embodiment, the stripping vessel or reaction vessel is a packed vessel, e.g. a packed column, configured to operate in countercurrent flow or cocurrent flow mode, using a liquid or gas continuous phase.

In a further embodiment, the stripping vessel or reaction vessel is a falling film (wetted wall) column, in which liquid is in contact with the column wall, and gas phase flows through the centre of the column in either cocurrent or countercurrent flow mode.

In yet another embodiment the stripping vessel or reaction vessel can be a spray chamber, in which liquid droplets are contacted with a continuous gas phase in either cocurrent flow, countercurrent flow or cross-flow mode.

In a still further embodiment, a line mixer can be used, in which the gas and liquid phases are fed co-currently, with a gas or liquid continuous phase. This operation can also be used where the stripping fluid is an immiscible liquid.

In embodiments, more than one type of reaction vessel and/or separation vessel can be used, operating either in parallel or in series. They can operate in batch-mode, semi-batch mode or continuous mode. In embodiments, recycling of gas and/or liquid phases can take place.

Where the vessel is adapted with plates or trays, there can be one or more plate types selected from valve plates (ballast plates), cross-stream plates, sieve plates, kittel polygonal plates, performkontact plates and bubble cap plates.

Where the vessel is packed vessel or column, the packing can be random packing or structured packing. Randomly packed vessels or columns can comprise one or more types of packing selected from Raschig rings, pall rings, Berl saddles and Intalox packings. Columns with structured packing can comprise one or more of Mellapack, Kerpak, Pyrapack G and F, and Rombapak. Packing materials can be metallic or ceramic.

For continuous gas-phase separation, the reaction or separation vessel can be suitably adapted with nozzles to produce a fine spray of droplets. In embodiments, cyclone stripping can be used where liquid droplets are injected into a high velocity rotating gas.

In embodiments, Venturi loop reactors or liquid jet loop reactors can be used can be used. In embodiments, film stripping can be used.

In embodiments, a membrane vessel can be used to allow selective permeation of $CO_2$ across a membrane, e.g. a hollow fibre membrane or a flat sheet membrane. The permeate side can optionally be held at a lower total pressure than the reaction mixture-containing containing side. A stripping fluid (e.g. stripping gas) can be fed to the permeate side to flush the permeated $CO_2$. In other embodiments, a $CO_2$ absorbing fluid can be fed to the permeate side, e.g. a fluid comprising an amine compound selected from the group of primary amines, cyclic secondary amines, and bicyclic tertiary amines referred to above.

Preferably, packed columns or tray-adapted vessels or columns are used. In embodiments, rotating packed beds can be used (so-called "HiGee" technology).

Preferably, the stripping vessel is also the reaction vessel.

Details of suitable vessels can be found in Ullmann's Encyclopedia of Industrial Chemistry, in the chapter Absorption, 2. Design of Systems and Equipment, 2012, pp 73-90, by Manfred Kriebel, and also in James Fair et al., Gas Absorption and Gas-Liquid System Design, in Perry's Chemical Engineer's Handbook.

Stripping fluid (in particular stripping gas) can be supplied at pressures in excess of those of the reaction mixture, for example at least 0.1 bar above the reaction mixture pressure, for example at least 0.5 bar or at least 1 bar above the reaction mixture pressure. For example, if the reaction mixture is maintained at atmospheric pressure, then the stripping fluid (e.g. stripping gas) can be supplied at a pressure of at least 0.1 barg (bar-gauge), for example at least 0.5 barg or at least 1 barg. The maximum pressure of stripping fluid supply will depend on the tolerances of the process equipment used, although typically it will be no more than 20 bar above the reaction mixture pressure.

The C02-containing stripping fluid removed from the CO2 removal step can, for example, comprise from 1 to 99 mol. % CO2. In other embodiments, the stripping fluid may comprise 1-80 mol. % CO2, or 1-60 mol. % CO2. In some embodiments, the effluent from the CO2 removal step may comprise 1-40 mol. % CO2, or 1-20 mol. % CO2. Lower CO2 contents make for more efficient stripping, but also for the use of more stripping gas. It is within the scope of the skilled person to find an appropriate balance between these parameters.

Where a stripping gas is used, the flow rate is typically at least 1 m3 per 1 m3 reactor volume per hour (at reaction temperature and pressure), and generally at most 100 m3 per 1 m3 reactor volume per hour (at reaction temperature and pressure). In addition to the stripping fluid provided to the stripping vessel, the stripping flow rate can be generated in part by evaporation of a liquid inside the reactor vessel, resulting in in situ generation of stripping gas. The ranges above also apply to this embodiment.

In embodiments, at least 20 mol %, for example at least 28 mol %, of the cyclic alkylene urea moieties are decarbonylated to corresponding diamine groups. In further embodiments, the yield of fully decarbonylated alkylene amines corresponding to the cyclic alkylene urea compounds is at least 20 mol %, for example at least 28 mol %.

The invention is illustrated by the following examples, without being limited thereto or thereby.

EXPERIMENTAL

The experiments 1 and 2 below were performed using a 2 liter pressure vessel equipped with a condenser, a pressure regulator, a gas distributor and a mixer. In each experiment, the vessel was operated at 250° C. The pressure in the reaction vessel and the condenser was kept constant at 30 bara using the pressure regulator. The top temperature of the condenser was kept at 30° C. During the reaction the mixture was stirred continuously, and was continuously contacted with $N_2$ gas supplied to the reactor vessel using the gas distributor. Gasses or vapors that were produced or fed to the system during the reaction in excess of 30 bara were allowed to escape the reactor via the condenser and the pressure regulator. The gas distributor was a sparger/glass frit, closely matching a cross-flow gas-liquid contact mode.

Experiment 1: DUTETA—CO2 removal—250° C.

A reaction mixture of 33 wt % of $H_2O$, 33 wt % of EDA and 33 wt % of DUTETA were prepared. The total weight of was 600 grams, and contained 2.0 mol of cyclic alkylene urea groups. During the experiment, the $N_2$ flow rate was 2 litres/minute, corresponding to 2 L/min/mol DUTETA, or 3.3 L/min/kg reaction mixture.

The reaction mixture was heated and held at 250° C. for 3 hours, after which the mixture was cooled down and analyzed by GC-FID (gas chromatography using a flame ionization detector). The mixture contained 0.26 mol L-TETA, with a yield of 25.7%.

Experiment 2—DUTETA—CO2 removal—250° C.

The same conditions as Experiment 1 were employed, except that the total weight of the reaction mixture was 750 grams, the mixture contained 2.5 mol of cyclic alkylene urea moieties, and the $N_2$ flow rate was 3 litres/min corresponding to 2.4 L/min/mol DUTETA, or 4.0 L/min/kg reaction mixture.

After the reaction, the resulting mixture contained 0.43 mol L-TETA, with a yield of 34.1%.

The results of Experiments 1 and 2 confirm that contacting a stripping fluid with the reaction mixture can improve removal of carbon dioxide from the reaction mixture. The results also confirm that higher stripping gas feed rates can improve the extent of conversion of cyclic alkylene ureas to corresponding cyclic alkyleneamines. Therefore, improving the extent of contact between a stripping fluid and the reaction mixture can help improve yields of desired alkylene amines.

Experiment 3 (Comparative): No CO2 Removal—DUTETA—175° C.—H2O/U Ratio of 53:1

A pressure vessel with a volume of 45 ml equipped with a mixer was used in this experiment. The temperature of the vessel was kept constant. During the reaction the mixture was continuously stirred.

A reaction mixture was prepared by mixing 4.5 grams of DUTETA and 21.7 grams of H2O. The molar ratio of H2O to urea moieties was 53:1. The mixture was kept at 175° C. for 5 hours in the reactor described above. Analysis by gas chromatography using a flame ionization detector (GC-FID analysis) showed that there was no conversion of DUTETA into L-TETA and that there was no removal of the initial urea-groups from the system.

This example applies conditions analogous to those used in U.S. Pat. No. 2,812,333. It can be seen that under these conditions it is not possible to convert DUTETA into L-TETA in a system without CO2 removal, even in the presence of large amounts of water.

Experiment 4 (Comparative): No CO2 Removal—DUTETA—270° C.—H2O/U Ratio of 4:1

The experimental set-up used in this example was a pressure vessel with a volume of 2000 ml equipped with a mixer. The temperature of the vessel was kept constant at the specified level. During the reaction the mixture was continuously stirred.

A reaction mixture was prepared by mixing 320 grams of DUTETA and 228 grams of H2O. The molar ratio of H2O to urea moieties was 4:1. The mixture was kept at 270° C. for 5 hours in the reactor described above. Analysis by gas chromatography using a flame ionization detector (GC-FID analysis) showed that there was no conversion of DUTETA into L-TETA and that there was no removal of the initial urea-groups from the system.

This example shows that it is not possible to convert DUTETA into L-TETA in a system without CO2 removal in the presence of limited amounts of water, not even at a temperature of 270° C.

Experiment 5 (Comparative): CO2 Removal—UAEEA—175° C.—H2O/U Ratio of 51:1

The experimental set-up used in this example was a pressure vessel with a volume of 2000 ml equipped with a condenser, a pressure regulator, a gas distributor and a mixer. The pressure in the reaction vessel and the condenser was kept constant at 30 bara using the pressure regulator. The top temperature of the condenser was kept between 30 and 60° C. using cooling water. During the reaction the mixture was continuously stirred and a constant flow of N2 gas was supplied to the reactor vessel using the gas distributor. Gasses or vapors that were produced or fed to the system during the reaction in excess of 30-32 bara were allowed to escape the reactor via the condenser and the pressure regulator unless otherwise specified in the example description.

A reaction mixture was prepared by mixing 85 grams of UAEEA and 604 grams of H2O. The molar ratio of H2O to urea moieties was 51:1. The mixture was kept at 175° C. for 3.6 hours in the reactor described above. The N2 gas flow used was ~3 L/min. Gasses or vapors that were produced or fed to the system during the reaction in excess of 12 bara were allowed to escape the reactor via the condenser and the pressure regulator.

Analysis by gas chromatography using a flame ionization detector (GC-FID analysis) showed that the conversion of UAEEA into AEEA was 4%. No detectable amount of the initial urea-groups was removed from the system.

This example shows that the conditions of U.S. Pat. No. 2,812,333 do not yield removal of urea groups even when CO2 is removed from the system.

Experiment 6: Conversion of DUTETA at Different Water to Urea Ratios with CO2 Removal The experimental set-up used was a pressure vessel with a volume of 2000 ml equipped with a condenser, a pressure regulator, a gas distributor and a mixer. The pressure in the reaction vessel and the condenser was kept constant at 30 bara using the pressure regulator. The top temperature of the condenser was kept between 30 and 60° C. During the reaction the mixture was continuously stirred and a constant flow of N2 gas was supplied to the reactor vessel using the gas distributor. Gasses or vapors that were produced or fed to the system during the reaction in excess of 30 bara were allowed to escape the reactor via the condenser and the pressure regulator.

Reaction mixtures were prepared containing DUTETA and water, with varying H2O to urea moiety ratios. In each experiment, the mixture was kept at 270° C. The N2 gas flow used was ~2 L/min. The reaction time was selected such in each experiment that the removal rate could be calculated with reasonable accuracy. The reaction mixtures were analysed by gas chromatography using a flame ionization detector (GC-FID analysis). The results are presented in Table 1.

TABLE 1

|  | Example 6.1 | Example 6.2 | Example 6.3 | Example 6.4 Comp |
|---|---|---|---|---|
| $H_2O/U$ (mol/mol) | 4 | 10 | 1 | 50 |
| Pressure (bar) | 35 | 34 | 34 | 34 |
| Temperature (C.) | 270 | 270 | 270 | 270 |
| Reaction time (hr) | 5.3 | 6.7 | 19.2 | 6.6 |
| N2 flow (L/min) | 2 | 2 | 2 | 2 |
| Results |  |  |  |  |
| Removal rate (mol/kg/hr) | 0.54 | 0.39 | 0.22 | 0.11 |
| U-removal | 70% | 73% | 49% | 73% |
| L-TETA yield | 54% | 51% | 21% | 25% |
| Selectivity (L-TETA yield/ U-removal) | 77% | 71% | 44% | 34% |

In Table 1, Examples 6.1, 6.2, and 6.3 are according to the invention. They show that operation at water to urea moiety molar ratios of 4:1, 10:1, and 1:1 result in a substantial removal of urea groups with a good selectivity to L-TETA. Contrary to expectations, the presence of more water in Comparative Experiment 6.4 (H2O/U molar ratio is 50:1) leads to a lower selectivity for L-TETA, and also to a lower removal rate.

Experiment 7: CO2 Removal—UDETA—Water to Urea Ratio of 4:1

A reaction mixture was prepared by mixing 350 grams of UDETA and 191 grams of H2O. The molar ratio of H2O to urea moieties was 4:1. The mixture was kept at 270° C. for 5.8 hours in the reactor described above. The N2 gas flow used was ~4 L/min. Analysis by gas chromatography using a flame ionization detector (GC-FID analysis) showed that the conversion of UDETA into DETA was 55% and that 60% of the initial urea-groups were removed from the system. The average removal rate was 0.62 mol/kg/hr.

Experiment 8: CO2 Removal—UAEEA at a Water to Urea Ratio of 4:1

A reaction mixture was prepared by mixing 350 grams of UAEEA and 188 grams of H2O. The molar ratio of H2O to urea moieties was 4:1. The mixture was kept at 250° C. for 4.2 hours in the reactor described above. The N2 gas flow used was ~2 L/min. Analysis by gas chromatography using a flame ionization detector (GC-FID analysis) showed that the conversion of UAEEA into AEEA was 42% and that 38% of the initial urea-groups were removed from the system. The average removal rate was 0.45 mol/kg/hr.

Experiment 9: CO2 Removal—UAEEA at a Water to Urea Ratio of 0.5:1

A reaction mixture was prepared by mixing 500 grams of UAEEA and 33 grams of H2O. The molar ratio of H2O to urea moieties was 0.5:1. The mixture was kept at 250° C. for 4.25 hours in the reactor described above. The N2 gas flow used was ~1.5 L/min. Gasses or vapors that were produced or fed to the system during the reaction in excess of 20 bara were allowed to escape the reactor via the condenser and the pressure regulator.

Analysis by gas chromatography using a flame ionization detector (GC-FID analysis) showed that the conversion of UAEEA into AEEA was 13% and that 13% of the initial urea-groups were removed from the system. The average removal rate was 0.23 mol/kg/hr.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

Abbreviations Used

AEEA aminoethylethanolamine, or 2-[(2-aminoethyl)amino]ethanol
AEP N-aminoethylpiperazine
CMEA 1,3-oxazolidin-2-one
DABCO 1,4-diazabicyclo[2.2.2]octane
DAEP N,N'-diaminoethylpiperazine
DETA diethylenetriamine, or N-(2-aminoethyl)-1,2-ethanediamine
DETA-PS diethylenetriamine linked to a solid polystyrene DUTETA 1,2-bis(ethyleneurea)ethane or 1,1'-(1,2-ethanediyl)di(2-imidazolidinone)
DUTEPA tetraethylenepentamine containing two cyclic urea groups—see FIG. 1
EDA ethylenediamine, or 1,2-diaminoethane
E2U 1,3-diethylurea
EU ethyleneurea, or 2-imidazolidinone
MEA ethanolamine, or 2-aminoethanol
MeEDA methylethylenediamine
PEHA pentaethylenehexamine
PEI polyethyleneimine
PIP piperazine
TAEA tris-aminoethylamine
TEPA tetraethylenepentamine
TETA triethylenetetramine (L-TETA refers specifically to linear-TETA)
UAEEA N-(2-hydroxyethyl)-ethyleneurea, or 1-(2-hydroxyethyl)-imidazolidin-2-one
UDETA N-(2-hydroxyethyl)-ethyleneurea, or 1-(2-aminoethyl)-imidazolidin-2-one
UTETA TETA containing a cyclic urea group—See FIG. 1
U1TETA UTETA with the cyclic urea group on one end of the molecule—See FIG. 1
U2TETA UTETA with the cyclic urea group in the centre of the molecule—See FIG. 1
U1PEHA PEHA with the cyclic urea group on one end of the molecule
U2PEHA PEHA with an ethylamine group on one of the urea nitrogen atoms
U3PEHA PEHA with a $H_2N(CH_2)_2NH(CH_2)_2$ group on one of the nitrogen atoms

The invention claimed is:

1. A process for converting one or more cyclic alkylene urea compounds comprising one or more cyclic alkylene urea moieties into corresponding ethylene amines and carbon dioxide, the process comprising:
    contacting water with the one or more cyclic alkylene urea compounds comprising the one or more cyclic alkylene urea moieties in a reaction vessel at a temperature of from 150 to 400° C.,
    optionally in the presence of an amine compound selected from the group consisting of primary amines, cyclic secondary amines and bicyclic tertiary amines, the mole ratio of the water to the cyclic alkylene urea moieties being in a range of from 0.1 to 20, wherein at least a portion of the cyclic alkylene urea moieties are converted to corresponding alkylenediamine moieties and carbon dioxide,
    removing carbon dioxide from the liquid reaction mixture in a stripping vessel by feeding a stripping fluid to the stripping vessel, and
    removing a carbon dioxide-containing stripping fluid.

2. The process of claim 1, in which the stripping vessel is also the reaction vessel.

3. The process of claim 1, in which the stripping vessel is selected from the group consisting of packed vessels and columns vessels or columns comprising trays, falling film columns, spray chambers, line mixers, membrane vessel, venturi loop vessels, and liquid jet loop vessels.

4. The process of claim 3, in which the stripping vessel is:
    (i) a randomly packed vessel, optionally comprising one or more types of packing selected from Raschig rings, pall rings, Berl saddles and Intalox packings; or
    (ii) a vessel or column with structured packing; or
    (iii) a vessel or column adapted with plates or trays, optionally comprising one or more plate types selected from valve plates, cross-stream plates, sieve plates, kittel polygonal plates, performkontakt plates and bubble cap plates.

5. The process of claim 3, in which the stripping vessel is a rotating packed bed vessel.

6. The process of claim 3, in which:
    (i) the stripping vessel is adapted with plates, and is configured to operate in countercurrent flow or crossflow mode using a liquid or gas continuous phase; or
    (ii) the stripping vessel is a packed vessel, configured to operate in countercurrent flow or cocurrent flow mode, using a liquid or gas continuous phase; or
    (iii) the stripping vessel is a falling film column, in which liquid is in contact with the column wall, and gas phase flows through the centre of the column in either cocurrent or countercurrent flow mode; or
    (iv) the stripping vessel is a spray chamber, in which liquid droplets are contacted with a continuous gas phase in either cocurrent flow, countercurrent flow or cross-flow mode; or
    (v) the stripping vessel is a line mixer, in which the gas and liquid phases are fed co-currently, with a gas or liquid continuous phase.

7. The process of claim 3, in which the stripping vessel is a membrane vessel, in which $CO_2$ transfers across the membrane to a permeate side of the membrane.

8. The process of claim 1, in which contact between the stripping fluid and reaction mixture is achieved by cross-flow or countercurrent flow.

9. The process of claim 1, in which more than one type of vessel is used, operating either in parallel or in series, operating in batch-mode, semi-batch mode or continuous mode, and optionally involving recycling of gas and/or liquid phase.

10. The process of claim 1, in which the stripping fluid is a stripping gas, the stripping gas optionally being selected from one or more of the group consisting of nitrogen, argon, steam and helium.

11. The process of claim 1, in which the one or more cyclic alkylene ureas are selected from those of Formula I:

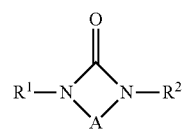

Formula I in which:
A is on each occurrence independently selected from $C_1$ to $C_3$ alkylene units, optionally substituted by one or more $C_1$ to $C_3$ alkyl groups;
$R^1$ and $R^2$ are each independently selected from $[A-X^1-]_q R^3$;
$R^3$ is on each occurrence independently selected from H or $C_1$ to $C_{20}$ alkyl groups, which are optionally substituted by one or two groups selected from —OH and —$NH_2$;
$X^1$ is on each occurrence independent selected from —O—, —$NR^3$—, groups of Formula II, and groups of Formula III:

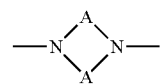

Formula II

-continued

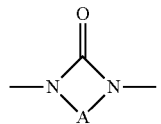

Formula III and each q is independently selected from a whole number in the range of from 0 to 20; and wherein the reaction produces one or more alkylenediamine moieties of Formula IV:

$R^4$—HN-A-NH—$R^5$    Formula IV in which:
$R^4$ and $R^5$ are each independently selected from -[A-$X^2$-]$_q R^3$;
$X^2$ is as defined above for $X^1$, and can also be selected from —NH-A-NH—; and
A, $R^3$ and q are as defined above.

12. The process of claim 11, in which one or more of the cyclic alkylene ureas are selected from the group consisting of EU (ethyleneurea), UDETA (the urea of diethylenetriamine), UTETA (the ureas of triethylenetetraamine), DUTETA (the diurea of triethylenetetramine), DUTEPA (the diurea of tetraethylenepentamine), UAEEA (the urea of aminoethylethanolamine), HE-UDETA (the urea of hydroxyethyl diethylenetriamine), HE-UTETA (the urea of hydroxyethyl triethylenetetraamine), and HE-DUTETA (the diurea of hydroxyethyl triethylenetetraamine), or any mixture of these.

13. The process of claim 1, in which one or more of the following conditions apply:
(i) the reaction is carried out at a pressure in the range of from 0.5 to 100 bar absolute;
(ii) the reaction time is in the range of from 1 minute to 24 hours;
(iii) the $CO_2$-containing stripping fluid removed from the stripping vessel comprises from 1 to 60 mol % $CO_2$;
(iv) the stripping fluid flow rate to the stripping vessel is at least 1 m³ per 1 m³ stripping vessel per hour.

14. The process of claim 11, in which one or more of the following apply:
(i) all occurrences of A are unsubstituted $C_2$-$C_3$ alkylene;
(ii) all occurrences of A are optionally substituted $C_2$ alkylene;
(iii) all occurrences of A are unsubstituted $C_2$ alkylene;
(iv) each $R^3$ is selected from H and $C_1$ to $C_3$ alkyl, optionally substituted with one $NH_2$ or OH group;
(v) each q is selected from a whole number from 0 to 3;
(vi) $X^1$ is selected from $NR^3$ and cyclic groups of Formula II and Formula III;
(vii) no more than one $X^1$ group is a cyclic group selected from groups of Formula II and Formula III;
(viii) $R^1$ is a hydrogen atom, $R^2$ contains an alkylene amine group -[A-$NR^3$-]$_q$- where q is at least 1; and/or
(ix) in Formula IV, $X^2$ is selected from —O—, —$NR^3$— and —NH-A-NH—.

* * * * *